(12) United States Patent
Hasegawa et al.

(10) Patent No.: US 10,041,831 B2
(45) Date of Patent: Aug. 7, 2018

(54) FLUORESCENT LIGHT PHANTOM DEVICE AND FLUORESCENT LIGHT IMAGING METHOD

(71) Applicant: HAMAMATSU PHOTONICS K.K., Hamamatsu-shi, Shizuoka (JP)

(72) Inventors: Kenjiro Hasegawa, Okayama (JP); Mitsuharu Miwa, Hamamatsu (JP); Takahiro Shikayama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 197 days.

(21) Appl. No.: 14/355,588

(22) PCT Filed: Oct. 18, 2012

(86) PCT No.: PCT/JP2012/076976
§ 371 (c)(1),
(2) Date: May 1, 2014

(87) PCT Pub. No.: WO2013/065498
PCT Pub. Date: May 10, 2013

(65) Prior Publication Data
US 2014/0303496 A1    Oct. 9, 2014

(30) Foreign Application Priority Data

Nov. 2, 2011    (JP) ................. 2011-241650

(51) Int. Cl.
*G01J 1/58* (2006.01)
*A61B 5/00* (2006.01)
(Continued)

(52) U.S. Cl.
CPC .............. *G01J 1/58* (2013.01); *A61B 5/0071* (2013.01); *A61B 5/0261* (2013.01); *A61B 90/39* (2016.02);
(Continued)

(58) Field of Classification Search
CPC ............ A61B 19/54; A61B 2019/5441; A61B 2560/0233; A61B 5/0071; A61B 5/0261
See application file for complete search history.

(56) References Cited

U.S. PATENT DOCUMENTS 7,054,002 B1 *  5/2006  Sevick-Muraca ..... G01J 3/4406
                                          250/459.1
7,919,744 B2    4/2011  Resch-Genger et al.
(Continued)

FOREIGN PATENT DOCUMENTS

CN    1773258       5/2006
EP    1243925 A2    9/2002
(Continued)

OTHER PUBLICATIONS

Yukio Ueda et al., "3-D Imaging of a Tissue-like Phantom by Near Infrared Light," Dai 17 Kai Hihakai Keisoku Symposium Koen Yoshishu, 2001, pp. 115-118, including English translation.

Primary Examiner — Baisakhi Roy
(74) Attorney, Agent, or Firm — Drinker Biddle & Reath LLP

(57) ABSTRACT

The fluorescent light phantom device 1 is provided with: a phantom support 10 having fluorescent light phantom containers 1b, 1c, 1d and 1e; and fluorescent light phantoms 12, 13, 14 and 15 which are constituted of a medium that reproduces at least one of light scattering and light absorption of an object to be measured and a fluorescent coloring matter contained in the medium of a predetermined concentration and are stored in the fluorescent light phantom containers 1b, 1c, 1d and 1e.

7 Claims, 7 Drawing Sheets

(51) Int. Cl.
*G01N 21/27* (2006.01)
*A61B 5/026* (2006.01)
*A61B 90/00* (2016.01)
*G01N 21/64* (2006.01)

(52) U.S. Cl.
CPC .... *G01N 21/278* (2013.01); *A61B 2090/3941* (2016.02); *A61B 2560/0233* (2013.01); *G01N 21/6456* (2013.01)

(56) References Cited

U.S. PATENT DOCUMENTS

| | | | |
|---|---|---|---|
| 2002/0072677 A1* | 6/2002 | Sevick-Muraca | A61B 5/0059 600/473 |
| 2004/0196455 A1 | 10/2004 | Ermantraut et al. | |
| 2006/0056580 A1* | 3/2006 | Frangioni | G01N 23/223 378/18 |
| 2006/0060931 A1 | 3/2006 | Cochet et al. | |
| 2006/0063274 A1 | 3/2006 | Schremp et al. | |
| 2008/0080781 A1 | 4/2008 | Pote et al. | |
| 2009/0080600 A1 | 3/2009 | Keller et al. | |
| 2010/0261811 A1* | 10/2010 | Thomas | G01N 21/6458 524/1 |
| 2011/0042580 A1 | 2/2011 | Wilson et al. | |
| 2011/0062318 A1* | 3/2011 | Bisaillon | G09B 23/285 250/252.1 |

FOREIGN PATENT DOCUMENTS

| | | |
|---|---|---|
| EP | 1 584 285 | 10/2005 |
| JP | H08-219994 A | 8/1996 |
| JP | 2000-089663 A | 3/2000 |
| JP | 2001-008941 A | 1/2001 |
| JP | 2002-272498 A | 9/2002 |
| JP | 2005-300540 A | 10/2005 |
| JP | 2006-043002 A | 2/2006 |
| JP | 2006-510916 A | 3/2006 |
| JP | 4091437 B2 | 5/2008 |
| JP | 2008-522158 A | 6/2008 |
| JP | 2009-524826 A | 7/2009 |
| JP | 2010-515031 A | 5/2010 |
| JP | 2011-069716 A | 4/2011 |
| JP | 2011-516864 A | 5/2011 |
| WO | WO 97/035513 | 10/1997 |
| WO | WO 2008/109709 | 9/2008 |
| WO | WO 2010/128090 | 11/2010 |
| WO | WO 2011/050441 | 5/2011 |

\* cited by examiner

FLUORESCENT LIGHT PHANTOM DEVICE AND FLUORESCENT LIGHT IMAGING METHOD

TECHNICAL FIELD

The invention relates to a fluorescent light phantom device and a fluorescent light imaging method.

BACKGROUND ART

In skin flap surgery in the field of plastic surgery, it is known that the presence or absence of blood flow in a transplanted living body tissue significantly affects recuperation after surgery. As a method for determining the presence or absence of blood flow, a method is known which is for determining the presence or absence of blood flow by injecting an indocyanine green (hereinafter referred to as "ICG") agent into a patient, then irradiating a target tissue with near-infrared light, and observing the tissue with a camera. Calibration auxiliary means described in Patent Literature 1 is known as an example of calibration auxiliary means for normalizing measurement results in such a blood flow presence/absence determining method. The calibration auxiliary means described in Patent Literature 1 is prepared by dissolving an ICG coloring matter and albumin protein into water and impregnating a carrier sheet with the solution.

CITATION LIST

Patent Literature

Patent Literature 1: Japanese Patent Application Laid-Open No. 2005-300540

SUMMARY OF INVENTION

Technical Problem

However, the calibration auxiliary means described in Patent Literature 1 has the following problems. That is, it is difficult to adjust precisely the content concentration of a fluorescent coloring matter, since a carrier sheet such as paper or cloth is impregnated with solution including the fluorescent coloring matter in a manufacturing process step of the calibration auxiliary means. Moreover, there is concern over deterioration of fluorescence characteristics caused by denaturation of protein, since the fluorescent coloring matter is combined with the albumin protein in the calibration auxiliary means. Due to such reasons, it is difficult to evaluate quantitatively the content concentration of a fluorescent coloring matter in an object to be measured, using such calibration means.

The present invention has been made for the purpose of solving the above problems, and an objective thereof is to provide a fluorescent light phantom device and a fluorescent light imaging method, which make it possible to evaluate quantitatively the concentration of a fluorescent coloring matter in an object to be measured.

Solution to Problem

In order to achieve such an objective, a fluorescent light phantom device according to an aspect of the present invention comprises: a phantom support having a fluorescent light phantom container; and a fluorescent light phantom, which is constituted of a medium that reproduces at least one of light scattering and light absorption of an object to be measured and a fluorescent coloring matter contained in the medium at a predetermined concentration and is stored in the fluorescent light phantom container.

In a fluorescent light phantom device according to an aspect of the present invention which is provided with a fluorescent light phantom having a content concentration of a fluorescent coloring matter that is a predetermined concentration, it becomes possible to compare the concentration of a fluorescent coloring matter in an object to be measured with the luminance of the fluorescent coloring matter in the fluorescent light phantom of the present invention and evaluate quantitatively the concentration by irradiating the object and the fluorescent light phantom with near-infrared light and comparing the luminance of fluorescent light from the object with the luminance of fluorescent light from the fluorescent light phantom for observation.

Moreover, in a fluorescent light phantom device according to an aspect of the present invention, the phantom support may have a plurality of fluorescent light phantom containers, the fluorescent light phantom may be stored in each of a plurality of fluorescent light phantom containers, and the concentration of the fluorescent coloring matter contained in a fluorescent light phantom may be different in each fluorescent light phantom. In such a case wherein the concentration of the fluorescent coloring matter is different in each of a plurality of fluorescent light phantoms, it becomes possible to evaluate more quantitatively the concentration of a fluorescent coloring matter in an object to be measured by comparing the luminance of fluorescent light from the object with the luminance of fluorescent light from a plurality of fluorescent light phantoms for observation.

Moreover, a fluorescent light phantom device according to an aspect of the present invention comprises: a phantom support having a fluorescent light phantom container; and a fluorescent light phantom stored in the fluorescent light phantom container, and the fluorescent light phantom has: a surface layer dummy, which is constituted of a medium that reproduces at least one of light scattering and light absorption of an object to be measured and is disposed at a surface layer of the fluorescent light phantom container; a deep layer dummy, which is constituted of the medium and is disposed at a deep layer of the fluorescent light phantom container; and a tabular phantom, which is constituted of the medium and a fluorescent coloring matter contained in the medium and is disposed at the fluorescent light phantom container to be held between the surface layer dummy and the deep layer dummy.

In a fluorescent light phantom device according to an aspect of the present invention, a tabular phantom is disposed between a surface layer dummy and a deep layer dummy, which are constituted of a medium that reproduces light scattering and light absorption of an object to be measured. Accordingly, even when scattering or light absorption occurs, it is possible to evaluate correctly the presence or absence of a fluorescent coloring matter in an object to be measured on the basis of a difference in the thickness of skin, fat or muscle of the object by irradiating the object and a fluorescent light phantom device of the present invention with near-infrared light and comparing the luminance of fluorescent light from the object with the luminance of fluorescent light from the fluorescent light phantom for observation.

Moreover, in a fluorescent light phantom device according to an aspect of the present invention, the phantom support may have a plurality of fluorescent light phantom containers, the fluorescent light phantom may be stored in each of a plurality of fluorescent light phantom containers, and the tabular phantoms may have equivalent thicknesses in the respective fluorescent light phantoms, may contain the fluorescent coloring matter of equivalent concentrations, and may be disposed at different depths in the respective fluorescent light phantoms. In such a case, tabular phantoms, which have equivalent thicknesses and contain the fluorescent coloring matter of equivalent concentrations, are disposed at different depths in the respective fluorescent light phantoms. Moreover, a tabular phantom is disposed between a surface layer dummy and a deep layer dummy, which are constituted of a medium that reproduces light scattering and light absorption of an object to be measured. Accordingly, even when scattering or light absorption occurs, it is possible to evaluate much more precisely the concentration of a fluorescent coloring matter in an object to be measured on the basis of a difference in the thickness of skin, fat or muscle of the object by irradiating the object and a fluorescent light phantom device of the present invention with near-infrared light and comparing the luminance of fluorescent light from the object with the luminance of fluorescent light from the fluorescent light phantom for observation.

Moreover, a fluorescent light phantom device according to an aspect of the present invention is characterized in that the above fluorescent light phantom devices in which a plurality of fluorescent light phantom containers are arranged in a row are arranged in a plurality of rows so that fluorescent light phantoms are arranged in a matrix form, and the concentration of the fluorescent coloring matter contained in a tabular phantom is different for each row.

In a fluorescent light phantom device according to an aspect of the present invention, the above fluorescent light phantom devices in which a plurality of fluorescent light phantom containers are arranged in a row are arranged in a plurality of rows so that fluorescent light phantoms are arranged in a matrix form, and the concentration of the fluorescent coloring matter contained in a tabular phantom is different for each row. Accordingly, it becomes possible to evaluate more precisely the concentration and the depth of a fluorescent coloring matter in an object to be measured by irradiating the object and a fluorescent light phantom device of the present invention with near-infrared light and comparing fluorescent light from the object with fluorescent light from the fluorescent light phantom device for observation.

Moreover, in a fluorescent light phantom device according to an aspect of the present invention, the phantom support and the fluorescent light phantom may be formed by epoxy resin. In such a case wherein the phantom support, the standard phantom and the fluorescent light phantom are formed by epoxy resin and are solidified, there is no concern that a medium will evaporate, and reliability of the fluorescent coloring matter concentration is secured for a long time.

Moreover, in a fluorescent light phantom device according to an aspect of the present invention, the phantom support may further have a standard phantom container and may further have a standard phantom, which is constituted of a medium that reproduces at least one of light scattering and light absorption of an object to be measured and is stored in the standard phantom container. In such a case, it becomes possible to evaluate more precisely the fluorescent light luminance without being affected by light scattering and light absorption by comparing the fluorescent light luminance of a standard phantom, which is constituted of a medium that reproduces light scattering and light absorption of an object to be measured with the fluorescent light luminance of a fluorescent light phantom, which is constituted of the above medium and a fluorescent coloring matter contained in the medium.

Moreover, in a fluorescent light phantom device according to an aspect of the present invention, the medium may include: at least one kind of scattered particles selected from the group consisting of titanium dioxide particles, silica particles, polymer minute particles, alumina, quartz glass minute particles and lipid minute particles; and at least one light absorbing substance selected from the group consisting of a pigment and a dye. Thus, light scattering and light absorption of an object to be measured are reproduced more accurately, and the fluorescent light luminance is measured more accurately.

Moreover, a fluorescent light phantom device according to an aspect of the present invention is attached to an object to be measured before use and comprises a fluorescent light phantom, which is constituted of a medium that reproduces at least one of light scattering and light absorption of the object and a fluorescent coloring matter contained in the medium at a predetermined concentration. In such a case wherein the fluorescent light phantom device is attached to an object to be measured before use, the fluorescent light phantom device can be bent along a curved surface. When the surface of an object to be measured is a curved surface, it becomes possible to measure more precisely the luminance of fluorescent light from the object by bending the fluorescent light phantom device along the surface of the object.

Moreover, in a fluorescent light phantom device according to an aspect of the present invention, a plurality of fluorescent light phantoms may be provided, and the concentration of the fluorescent coloring matter contained in a fluorescent light phantom may be different in each fluorescent light phantom. In such a case wherein the concentration of the fluorescent coloring matter is different in each of a plurality of fluorescent light phantoms, it becomes possible to evaluate more quantitatively the concentration of a fluorescent coloring matter in an object to be measured by comparing the luminance of fluorescent light from the object with the luminance of fluorescent light from a plurality of fluorescent light phantoms for observation.

Moreover, in a fluorescent light phantom device according to an aspect of the present invention, the fluorescent light phantom may be formed by polyurethane resin or silicone resin. In such a case wherein the fluorescent light phantom is formed in semi-solidified gel form, it becomes possible to bend the fluorescent light phantom device along the surface of an object to be measured and it also becomes possible to measure more precisely the luminance of fluorescent light from the object.

Moreover, in a fluorescent light phantom device according to an aspect of the present invention, the fluorescent coloring matter may be ICG. Thus, it is possible in fluorescence observation for a living body as an object to be measured to observe a living body deep site while being hardly affected by light absorption by blood, which absorbs light having a wavelength shorter than 600 nm, or water, which absorbs light having a wavelength longer than 1000 nm, since ICG, which has optical characteristics such as an excitation wavelength within the range of 750 nm to 810 nm and a fluorescence wavelength with the center at 840 nm, is used as the fluorescent coloring matter. Moreover, it is possible to inlet ICG, which is harmless to a living body, into a living body and perform fluorescence observation using a fluorescent light phantom device according to an aspect of the present invention.

Moreover, a fluorescent light imaging method according to an aspect of the present invention comprises the following steps of: introducing a fluorescent coloring matter into a living body, disposing a fluorescent light phantom device of the present invention in the vicinity of the living body; irradiating the living body and the fluorescent light phantom device with excitation light; and detecting near-infrared fluorescent light from the fluorescent coloring matter introduced into the living body and the fluorescent coloring matter included in the fluorescent light phantom.

With a fluorescent light imaging method according to an aspect of the present invention wherein a fluorescent light phantom device, which is provided with a fluorescent light phantom having a content concentration of a fluorescent coloring matter that is a predetermined concentration, is irradiated together with a living body which is an object to be measured, it is possible to evaluate quantitatively the concentration of a fluorescent coloring matter in the living body.

Advantageous Effects of Invention

With the present invention, a fluorescent light phantom device and a fluorescent light imaging method which make it possible to evaluate quantitatively the concentration of a fluorescent coloring matter in an object to be measured are obtained.

DESCRIPTION OF EMBODIMENTS

The following description will explain preferred embodiments of a fluorescent light phantom device according to the present invention with reference to the drawings. It is to be noted that identical elements in the respective figures are denoted by identical symbols and repetition in a description will be omitted.

First Embodiment

Figure 1:
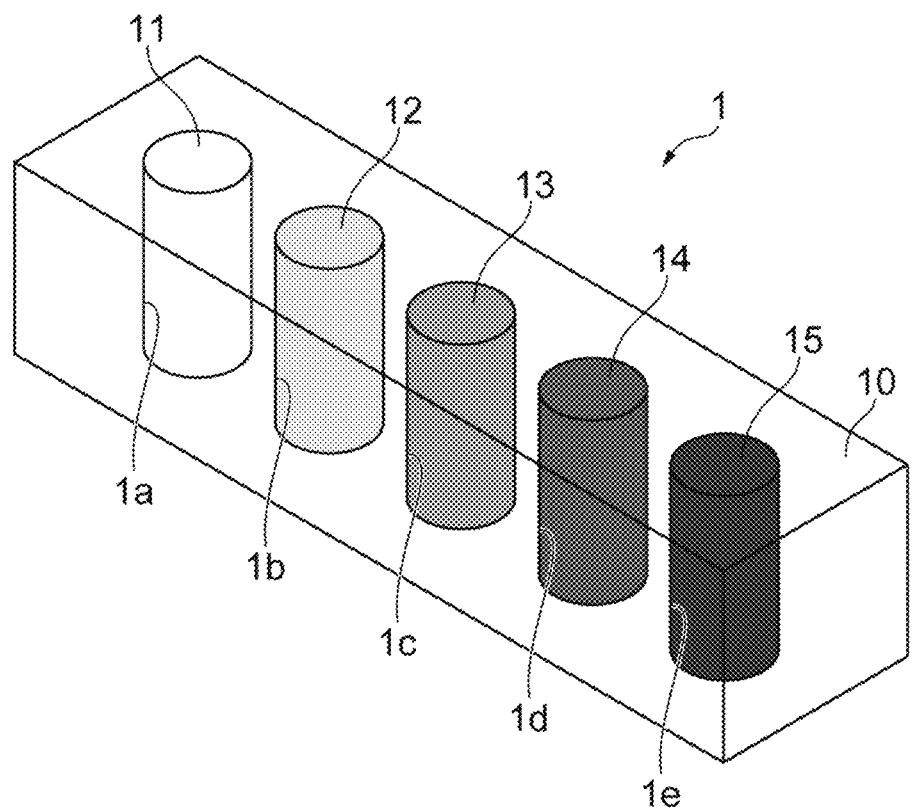
FIG. 1 is a perspective view for illustrating the structure of a fluorescent light phantom device according to a first embodiment.

FIG. 1 is a perspective view for illustrating the structure of a fluorescent light phantom device 1 according to a first embodiment. As illustrated in the figure, the fluorescent light phantom device 1 is composed of a phantom support 10, a standard phantom 11 and a plurality of (four in the present embodiment) fluorescent light phantoms 12, 13, 14 and 15.

The phantom support 10 has a standard phantom container 1a to be used for storing the standard phantom 11, and a plurality of (four in the present embodiment) fluorescent light phantom containers 1b, 1c, 1d and 1e to be used for storing the fluorescent light phantoms 12, 13, 14 and 15. Moreover, the phantom support 10 is formed by epoxy resin.

The standard phantom 11 is constituted of a medium which reproduces light scattering and light absorption of an object to be measured such as a living body, for example. Specifically, a medium which constitutes the standard phantom 11 includes at least one kind of particles selected from the group consisting of titanium dioxide ($TiO_2$) particles, silica particles, polymer minute particles, alumina ($Al_2O_3$), quartz glass minute particles and lipid minute particles as scattered particles for reproducing light scattering. It is to be noted that a specific example of lipid minute particles is milk, Intralipid (registered trademark) or the like. Moreover, a medium which constitutes the standard phantom 11 includes at least one substance selected from the group consisting of a pigment and a dye as a light absorbing substance for reproducing light absorption. In the present embodiment, a medium which constitutes the standard phantom 11 is liquid obtained by mixing the above scattered particles and the above light absorbing substance with ethanol that functions as a solvent. The standard phantom 11 is stored in the standard phantom container 1a of the phantom support 10, and the standard phantom container 1a is sealed.

The fluorescent light phantoms 12, 13, 14 and 15 are constituted of the above medium and a fluorescent coloring matter contained in the medium of a predetermined concentration. In the present embodiment, ICG is used as the fluorescent coloring matter. The concentration of ICG contained in the fluorescent light phantoms 12, 13, 14 and 15 is different for each of the fluorescent light phantoms 12, 13, 14 and 15. Moreover, in the present embodiment, the fluorescent light phantoms 12 13, 14 and 15 are arranged in a row and are lined up in the order from one having a lower content concentration of ICG to one having a higher content concentration of ICG. In the present embodiment, the fluorescent light phantoms 12, 13, 14 and 15 are liquid and are stored in the fluorescent light phantom containers 1b, 1c, 1d and 1e of the phantom support 10, and the fluorescent light phantom containers 1b, 1c, 1d and 1e are sealed.

Next, a fluorescent light imaging method which uses the fluorescent light phantom device 1 of the present embodiment will be explained. First, ICG is introduced as a fluorescent coloring matter into a living body which is an object to be measured. Next, the fluorescent light phantom device 1 is disposed in the vicinity of the living body. The living body and the fluorescent light phantom device 1 are then irradiated with excitation light using near-infrared light having an excitation wavelength within the range of 750 nm to 810 nm. Here, near-infrared fluorescent light having a fluorescence wavelength with the center at a wavelength of 840 nm is generated from the ICG introduced into the living body. Moreover, near-infrared fluorescent light having the same wavelength is also generated from the fluorescent light phantoms 12, 13, 14 and 15 of the fluorescent light phantom device 1. Here, the intensity of near-infrared fluorescent light to be generated corresponds to the content concentration of ICG in the living body and the fluorescent light phantoms 12, 13, 14 and 15, and the intensity of near-infrared fluorescent light to be generated becomes higher as the content concentration of ICG becomes higher. The near-infrared fluorescent light is detected with a near-infrared camera, for example. It is possible to perform a fluorescent light imaging process by performing image processing for the detected near-infrared fluorescent light with a heretofore known method.

Figure 2:
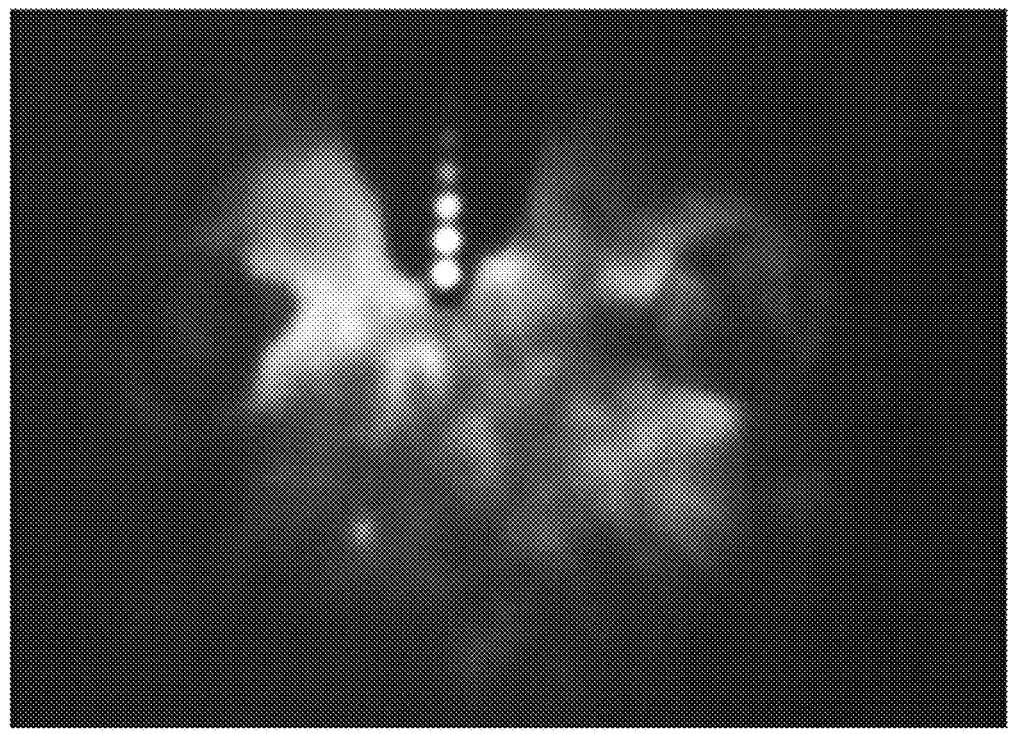
FIG. 2 is a photograph of a living body and a fluorescent light phantom device according to the first embodiment, which is taken with a near-infrared camera.

FIG. 2 shows a photograph which is an example of the result of fluorescent light imaging with the method described above. FIG. 2 is a photograph of a living body and the fluorescent light phantom device 1 according to the first embodiment, which was taken with a near-infrared camera. Shining points are lined up in a row in the vertical direction at a slightly upper side than the central part of FIG. 2. The brightness is different for each of the points, and a lower point is brighter. Since the brightness of a point corresponds to the content concentration of ICG in a fluorescent light phantom as described above, the fact that a lower point is brighter represents that the fact that a fluorescent light phantom corresponding to a lower point has a higher content concentration of ICG. Moreover, it becomes possible to correlate the content concentration of ICG to the brightness of a point on the basis of the brightness of the points lined up in a row, since the content concentration of ICG included in the fluorescent light phantom is known. That is, parts which shine at the same degree of brightness have the same level of content concentration of ICG.

Moreover, in FIG. 2, a white shining part is spread around the points, which represent fluorescent light from the fluorescent light phantoms and are lined up vertically. This represents fluorescent light generated from ICG introduced into a living body which is an object to be measured. It is possible to find the magnitude relationship between the concentration of ICG in the living body and the content concentration of ICG in the fluorescent light phantom, evaluate quantitatively the concentration of ICG in the living body, and evaluate quantitatively the presence or absence of blood flow, which includes ICG and flows in the living body, or the amount of the blood flow, for example, by comparing the intensity of fluorescent light from ICG in the living body with the intensity of fluorescent light of the fluorescent light phantom.

With the present embodiment which is provided with the fluorescent light phantoms 12, 13, 14 and 15 having a content concentration of the fluorescent coloring matter that is a predetermined concentration, it becomes possible to compare the concentration of a fluorescent coloring matter in an object to be measured with the luminance of a fluorescent coloring matter in the fluorescent light phantoms 12, 13, 14 and 15 and evaluate quantitatively the concentration by irradiating the object and the fluorescent light phantom device 1 of the present embodiment with near-infrared light and comparing the luminance of fluorescent light from the object with the luminance of fluorescent light from the fluorescent light phantoms 12, 13, 14 and 15 for observation.

Moreover, in the fluorescent light phantom device 1 wherein the content concentration of the fluorescent coloring matter is different for each of fluorescent light phantoms 12, 13, 14 and 15, it becomes possible to evaluate more quantitatively the concentration of a fluorescent coloring matter in an object to be measured by comparing the luminance of fluorescent light from the object with the luminance of fluorescent light from a plurality of fluorescent light phantoms 12, 13, 14 and 15 for observation.

Moreover, since the fluorescent light phantom device 1 has the standard phantom 11, it becomes possible to evaluate more precisely the fluorescent light luminance without being affected by light scattering and light absorption, by comparing the fluorescent light luminance of the standard phantom 11, which is constituted of a medium that reproduces light scattering and light absorption of an object to be measured, with the fluorescent light luminance of the fluorescent light phantoms 12, 13, 14 and 15, which are constituted of the above medium and a fluorescent coloring matter contained in the medium.

Moreover, in the fluorescent light phantom device 1 wherein the medium which constitutes the standard phantom 11 and the fluorescent light phantoms 12, 13, 14 and 15 includes at least one kind of scattered particles selected from the group consisting of titanium dioxide particles, silica particles, polymer minute particles, alumina, quartz glass minute particles and lipid minute particles and at least one light absorbing substance selected from the group consisting of a pigment and a dye, light scattering and light absorption of an object to be measured are reproduced more accurately and the fluorescent light luminance is measured more accurately.

Moreover, with a fluorescent image method according to the present embodiment wherein the fluorescent light phantom device 1 provided with a plurality of fluorescent light phantoms 12, 13, 14 and 15 having respectively different content concentrations of the fluorescent coloring matter is irradiated together with a living body which is an object to be measured, it is possible to evaluate quantitatively the concentration of a fluorescent coloring matter in the living body.

Moreover, in the fluorescent light phantom device 1 wherein ICG is used as the fluorescent coloring matter, it is possible in fluorescence observation for a living body as an object to be measured to observe a living body deep site while being hardly affected by light absorption by blood, which absorbs light having a wavelength shorter than 600 nm, or water, which absorbs light having a wavelength longer than 1000 nm, since ICG, which has optical characteristics such as an excitation wavelength within the range of 750 nm to 810 nm and a fluorescence wavelength with the center at 840 nm, is used as the fluorescent coloring matter.

It is to be noted that a solvent which constitutes the standard phantom and the fluorescent light phantoms in the present embodiment is not limited to ethanol, and methanol, dimethyl sulfoxide, water or the like can be used instead of ethanol. Moreover, a medium which constitutes the standard phantom 11 and the fluorescent light phantoms 12, 13, 14 and 15 does not necessarily include both of light scattering particles and a light absorbing substance but needs only to include at least one thereof.

Second Embodiment

Figure 3:
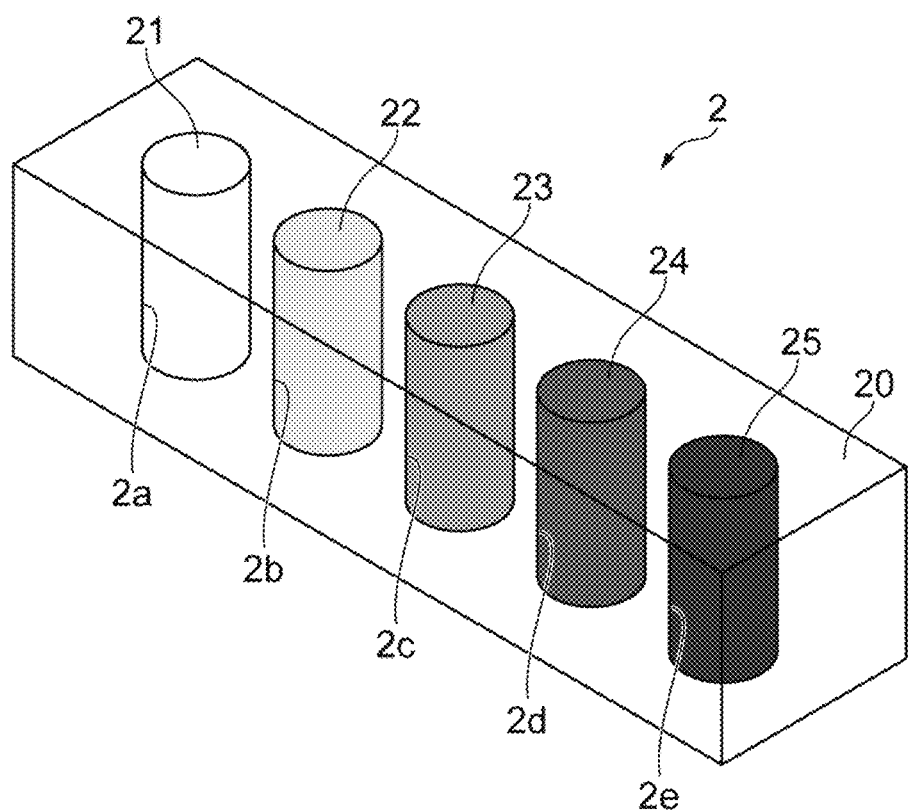
FIG. 3 is a perspective view for illustrating the structure of a fluorescent light phantom device according to a second embodiment.

Next, a second embodiment will be explained. FIG. 3 is a perspective view for illustrating the structure of a fluorescent light phantom device 2 according to the second embodiment. The fluorescent light phantom device 2 according to the second embodiment is different from the fluorescent light phantom device 1 according to the first embodiment in that a standard phantom 21 and fluorescent light phantoms 22, 23, 24 and 25 are formed by epoxy resin and are solidified. Accordingly, the difference from the first embodiment will be mainly explained.

The fluorescent light phantom device 2 is composed of a phantom support 20, the standard phantom 21 and the fluorescent light phantoms 22, 23, 24 and 25. The phantom support 20 is provided with a standard phantom container 2a to be used for storing the standard phantom 21, and fluorescent light phantom containers 2b, 2c, 2d and 2e to be used for storing the fluorescent light phantoms 22, 23, 24 and 25.

The standard phantom 21 is constituted of a medium which reproduces light scattering and light absorption as with the standard phantom 11 of the first embodiment. Substances similar to those of the first embodiment can be used as the light scattering particles and the light absorbing substance included in the medium. In the present embodiment, the medium is obtained by mixing light scattering particles and a light absorbing substance with ethanol and further mixing the liquid with epoxy resin so as to solidify the liquid.

The fluorescent light phantoms 22, 23, 24 and 25 are constituted of the above medium and ICG contained in the medium of a predetermined concentration. More specifically, the medium is formed by mixing light scattering particles and a light absorbing substance with ethanol, further dissolving ICG of a predetermined concentration, and mixing epoxy resin so as to solidify the liquid. The concentration of ICG contained in the fluorescent light phantoms 22 23, 24 and 25 is different for each of the fluorescent light phantoms 22, 23, 24 and 25. Moreover, in the present embodiment, the fluorescent light phantoms 22, 23, 24 and 25 are arranged in a row and are lined up in the order from one having a lower content concentration of ICG to one having a higher content concentration of ICG.

It is also possible to implement a fluorescent light imaging method similar to the method explained in the first embodiment by using the fluorescent light phantom device 2 having the above structure.

With the present embodiment, an effect similar to that of the first embodiment can be obtained. Furthermore, with the fluorescent light phantom device 2 wherein the standard phantom 21 and the fluorescent light phantoms 22, 23, 24 and 25 are formed by epoxy resin, the standard phantom 21 and the fluorescent light phantoms 22, 23, 24 and 25 are solidified, there is no concern that the medium will evaporate, and reliability of the fluorescent coloring matter concentration is secured for a long time.

Third Embodiment

Figure 4:
FIG. 4 is a plan view for illustrating the structure of a fluorescent light phantom device according to a third embodiment.

Next, a third embodiment will be explained. FIG. 4 is a plan view for illustrating the structure of a fluorescent light phantom device 3 according to the third embodiment. The fluorescent light phantom device 3 according to the third embodiment is composed of a standard phantom 31 and fluorescent light phantoms 32 and 33. Moreover, the fluorescent light phantom device 3 is attached to an object to be measured before use.

The standard phantom 31 is constituted of a medium which reproduces light scattering and light absorption of an object to be measured. Specifically, the medium is obtained by mixing ethanol, which includes light scattering particles and a light absorbing substance similar to those of the first embodiment mixed therein, with polyurethane resin. Since polyurethane resin is mixed with the medium, the standard phantom 31 is semi-solidified and formed in gel form.

The fluorescent light phantoms 32 and 33 are constituted of the above medium and ICG contained in the medium of a predetermined concentration. Accordingly, the fluorescent light phantoms 32 and 33 are also semi-solidified and are formed in gel form as with the standard phantom 31.

The fluorescent light phantom device 3 having the above structure is in a semi-solidified form which can be bent along a curved surface.

Figure 5:
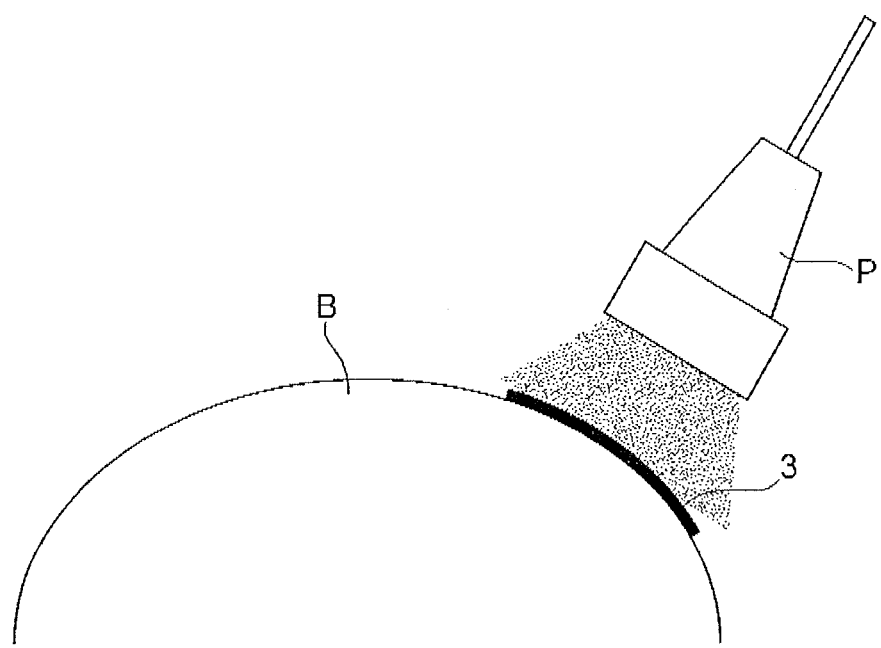
FIG. 5 is a schematic diagram for illustrating the usage of a fluorescent light phantom device according to the third embodiment.

The usage of the fluorescent light phantom device 3 having the above structure will be explained with reference to FIG. 5. FIG. 5 is a schematic diagram for illustrating the usage of the fluorescent light phantom device 3 according to the third embodiment. The surface of a living body B, which is an object to be measured, forms a convex curved surface. The fluorescent light phantom device 3 is bent along the surface of the living body B and is placed on the living body B. A near-infrared camera P is then brought close to from a direction perpendicular to the surface of the fluorescent light phantom device 3, and a photograph of the fluorescent light phantom device 3 and the living body is taken with the near-infrared camera P.

With the fluorescent light phantom device 3 having the above structure, effects similar to those of a case where the fluorescent light phantom device 1 according to the first embodiment is used are obtained. Moreover, in the fluorescent light phantom device 3 wherein the standard phantom 31 and the fluorescent light phantoms 32 and 33 are formed by polyurethane resin, it is possible to bend the fluorescent light phantom device along a curved surface. Therefore, when the surface of an object to be measured is a curved surface, it becomes possible to measure more precisely the luminance of fluorescent light from the object by bending the fluorescent light phantom device along the surface of the object.

It is to be noted that silicone resin, for example, may be used instead of polyurethane resin as resin to be used for semi-solidifying the fluorescent light phantom device 3 and forming the same in gel form in the present embodiment.

Fourth Embodiment

Figure 6:
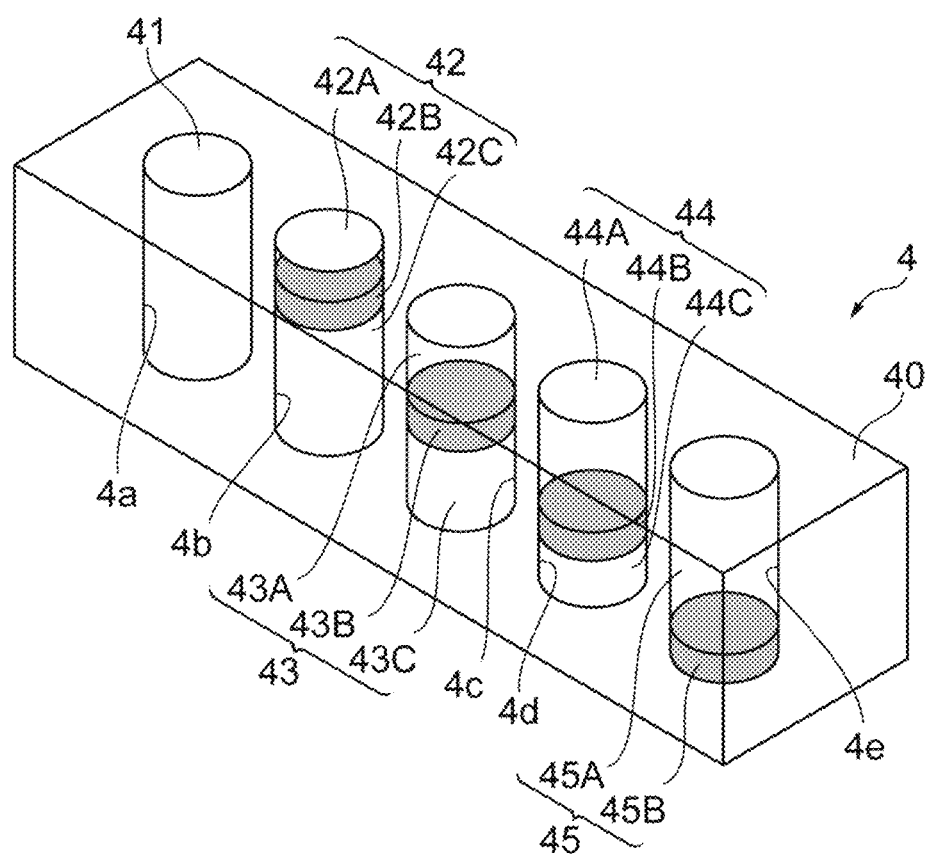
FIG. 6 is a perspective view for illustrating the structure of a fluorescent light phantom device according to a fourth embodiment.

Next, a fourth embodiment will be explained. FIG. 6 is a perspective view for illustrating the structure of a fluorescent light phantom device 4 according to the fourth embodiment. The fluorescent light phantom device 4 according to the fourth embodiment is composed of a phantom support 40, a standard phantom 41 and a plurality of (four in the present embodiment) fluorescent light phantoms 42, 43, 44 and 45. The phantom support 40 is provided with a standard phantom container 4a to be used for storing the standard phantom 41, and fluorescent light phantom containers 4b, 4c, 4d and 4e to be used for storing the fluorescent light phantoms 42, 43, 44 and 45.

The standard phantom 41 is constituted of a medium, which is obtained by mixing epoxy resin with ethanol including light scattering particles and a light absorbing substance mixed therein, and is formed in a solidified form as with the standard phantom 21 of the second embodiment.

The fluorescent light phantom 42 has a surface layer dummy 42A, a tabular phantom 42B and a deep layer dummy 42C. The surface layer dummy 42A is constituted of a medium which reproduces light scattering and light absorption of an object to be measured. Moreover, the surface layer dummy 42A is disposed at a surface layer of a fluorescent light phantom container 4b which is provided at the phantom support 40. The deep layer dummy 42C is constituted of the above medium and is disposed at a deep layer of the fluorescent light phantom container 4b. The tabular phantom 42B is constituted of the above medium and ICG contained in the medium as the fluorescent coloring matter. Moreover, the tabular phantom 42B is disposed at the fluorescent light phantom container 4b so as to be held between the surface layer dummy 42A and the deep layer dummy 42C.

Similarly, the fluorescent light phantom 43 has a surface layer dummy 43A, a tabular phantom 43B and a deep layer dummy 43C, and the tabular phantom 43B is disposed at the fluorescent light phantom container 4c so as to be held between the surface layer dummy 43A and the deep layer dummy 43C. The fluorescent light phantom 44 has a surface layer dummy 44A, a tabular phantom 44B and a deep layer dummy 44C, and the tabular phantom 44B is disposed at the fluorescent light phantom container 4d so as to be held between the surface layer dummy 44A and the deep layer dummy 44C. The fluorescent light phantom 45 is composed of a surface layer dummy 45A and a tabular phantom 45B. In the fluorescent light phantom 45, the tabular phantom 45B is disposed at the deepest part of the fluorescent light phantom container 4e, and a deep layer dummy is not provided.

In the present embodiment, the tabular phantoms 42B, 43B, 44B and 45B have equivalent thickness in the respective fluorescent light phantoms 42, 43, 44 and 45 and contain ICG of equivalent concentrations. Moreover, the tabular phantoms 42B, 43B, 44B and 45B are disposed at a different depth in each fluorescent light phantom. In the present embodiment, the fluorescent light phantoms 42, 43, 44 and 45 are arranged in a row and are constructed in such a manner that the depth where the tabular phantoms 42B, 43B, 44B and 45B are disposed becomes deeper in order.

It is also possible to implement a fluorescent light imaging method similar to the method explained in the first embodiment by using the fluorescent light phantom device 4 having the above structure.

With the present embodiment, the tabular phantom 42B is disposed between the surface layer dummy 42A and the deep layer dummy 42C, which are constituted of a medium that reproduces light scattering and light absorption of an object to be measured. Accordingly, even when scattering or light absorption occurs, it is possible to evaluate correctly the presence or absence of a fluorescent coloring matter in an object to be measured on the basis of a difference in the thickness of skin, fat or muscle of the object by irradiating the object and the fluorescent light phantom device 4 of the present embodiment with near-infrared light and comparing the luminance of fluorescent light from the object with the luminance of fluorescent light from the fluorescent light phantom for observation.

Moreover, in the fluorescent light phantom device 4 according to the present embodiment, the tabular phantoms 42B, 43B, 44B and 45B which have equivalent thicknesses and contain the fluorescent coloring matter of equivalent concentrations are disposed at a different depth in each of the fluorescent light phantoms 42, 43, 44 and 45 in such a case. Moreover, the tabular phantom 42B is disposed between the surface layer dummy 42A and the deep layer dummy 42C, which are constituted of a medium that reproduces light scattering and light absorption of an object to be measured. Accordingly, even when scattering or light absorption occurs, it is possible to evaluate much more precisely the concentration of a fluorescent coloring matter in an object to be measured on the basis of a difference in the thickness of skin, fat or muscle of the object by irradiating the object and the fluorescent light phantom device 4 of the present embodiment with near-infrared light and comparing the luminance of fluorescent light from the object with the luminance of fluorescent light from the fluorescent light phantoms 42, 43, 44 and 45 for observation.

Fifth Embodiment

Figure 7:
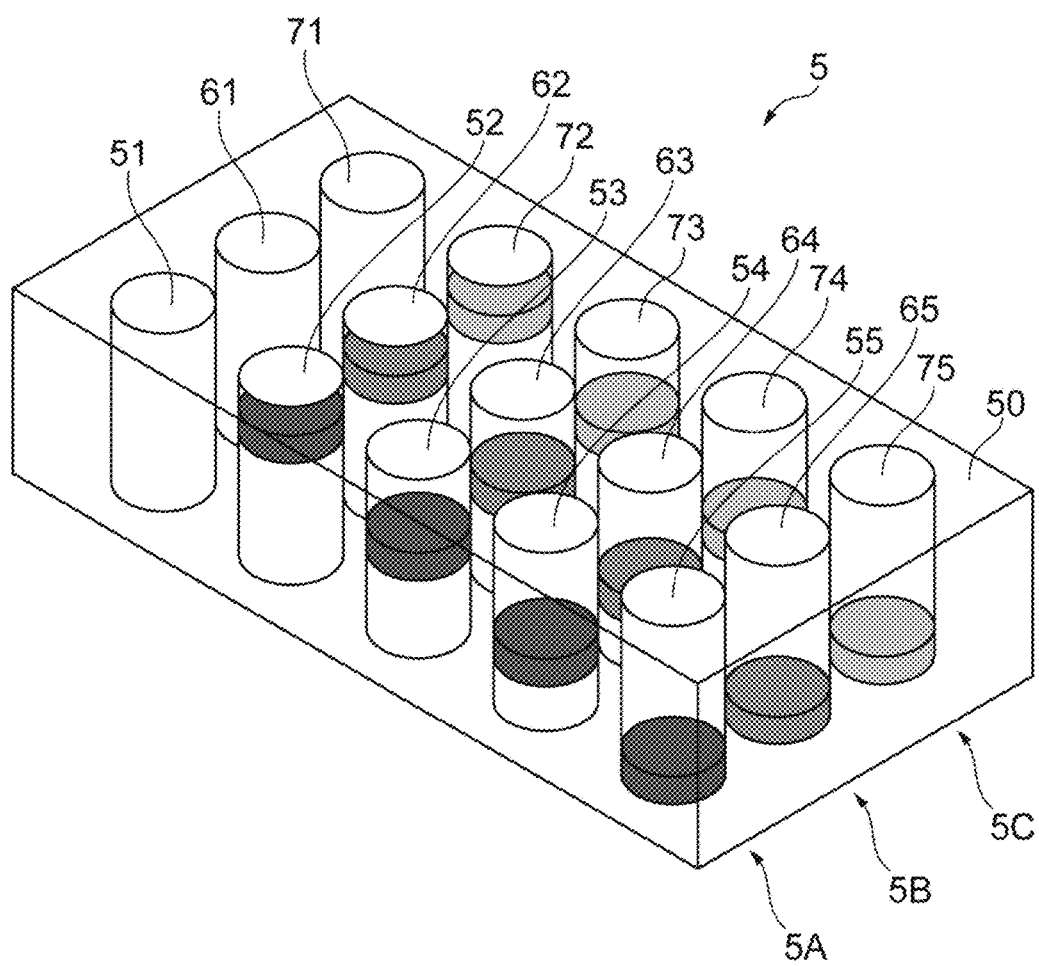
FIG. 7 is a perspective view for illustrating the structure of a fluorescent light phantom device according to a fifth embodiment.

Next, a fifth embodiment will be explained. FIG. 7 is a perspective view for illustrating the structure of a fluorescent light phantom device 5 according to the fifth embodiment. The fluorescent light phantom device 5 according to the fifth embodiment is composed of a phantom support 50, standard phantoms 51, 61 and 71, and fluorescent light phantoms 52, 53, 54, 55, 62, 63, 64, 65, 72, 73, 74 and 75. The standard phantoms 51, 61 and 71 are constituted of a medium, which is obtained by mixing epoxy resin with ethanol including light scattering particles and a light absorbing substance mixed therein, and is formed in a solidified form as with the standard phantom 41 according to the fourth embodiment.

The fluorescent light phantoms 52, 53, 54, 55, 62, 63, 64, 65, 72, 73, 74 and 75 respectively have a tabular phantom as with the fluorescent light phantoms 42, 43, 44 and 45 according to the fourth embodiment. Moreover, in the fluorescent light phantom device 5, the standard phantom 51 and the fluorescent light phantoms 52, 53, 54 and 55 are arranged in a row, the standard phantom 61 and the fluorescent light phantoms 62, 63, 64 and 65 are arranged in a row, and the standard phantom 71 and the fluorescent light phantoms 72, 73, 74 and 75 are arranged in a row. The tabular phantoms provided at the fluorescent light phantoms 52, 53, 54 and 55 have equivalent thicknesses, contain ICG of equivalent concentrations, and are provided at different depths. The tabular phantoms provided at the fluorescent light phantoms 62, 63, 64 and 65 have equivalent thicknesses, contain ICG of equivalent concentrations, and are provided at different depths. The tabular phantoms provided at the fluorescent light phantoms 72, 73, 74 and 75 have equivalent thicknesses, contain ICG of equivalent concentrations, and are provided at different depths. Here, the concentration of ICG contained in the fluorescent light phantoms 52, 62 and 72 are different from each other. Accordingly, the phantom support 50, the standard phantom 51 and the fluorescent light phantoms 52, 53, 54 and 55 compose a phantom device 5A of the fourth embodiment. Similarly, the phantom support 50, the standard phantom 61 and the fluorescent light phantoms 62, 63, 64 and 65 compose a phantom device 5B of the fourth embodiment, and the phantom support 50, the standard phantom 71 and the fluorescent light phantoms 72, 73, 74 and 75 compose a phantom device 5C of the fourth embodiment. That is, the fluorescent light phantom device 5 of the present embodiment can be considered as an assembly wherein the three fluorescent light phantoms devices 5A to 5C are arranged in a plurality of rows (arranged in three rows in the present embodiment). In the fluorescent light phantom device 5 wherein the three fluorescent light phantom devices 5A to 5C are arranged, the fluorescent light phantoms 52, 53, 54, 55, 62, 63, 64, 65, 72, 73, 74 and 75 are arranged in a matrix form. Moreover, the concentration of ICG contained in each fluorescent light phantom is different for each row.

It is also possible to implement a fluorescent light imaging method similar to the method explained in the first embodiment by using the fluorescent light phantom device 5 having the above structure.

With the present embodiment, the fluorescent light phantom device 5 is constructed in such a manner that fluorescent light phantom devices in which a plurality of fluorescent light phantom containers are arranged in a row are arranged in a plurality of rows so that fluorescent light phantoms are arranged in a matrix form, and the concentration of the fluorescent coloring matter contained in the tabular phantoms is different for each row. Accordingly, it becomes possible to evaluate more precisely the concentration and the depth of the fluorescent coloring matter in an object to be measured by irradiating the object and the fluorescent light phantom device 5 of the present embodiment with near-infrared light and comparing fluorescent light from the object with fluorescent light from the fluorescent light phantom device 5 for observation.

INDUSTRIAL APPLICABILITY

With the present invention, the fluorescent light phantom devices 1 to 5 and a fluorescent light imaging method, which make it possible to evaluate quantitatively the concentration of a fluorescent coloring matter in an object to be measured, are provided.

REFERENCE SIGNS LIST 1, 2, 3, 4, 5, 5A to 5C . . . Fluorescent Light Phantom Device, 1a, 2a, 4a . . . Standard Phantom Container, 1b to 1e, 2b to 2e, 4b to 4e . . . Fluorescent Light Phantom Container, 10, 20, 40, 50 . . . Phantom Support, 11, 21, 31, 41, 51 . . . Standard Phantom, 12, 13, 14, 15, 22, 23, 24, 25, 32, 33, 42, 43, 44, 45, 52, 53, 54, 55, 62, 63, 64, 65, 72, 73, 74, 75 . . . Fluorescent Light Phantom, 42A, 43A, 44A, 45A . . . Surface Layer Dummy, 42B, 43B, 44B, 45B, . . . Tabular Phantom, 42C, 43C, 44C . . . Deep Layer Dummy, B . . . Living Body, P . . . Near-infrared Camera

The invention claimed is:

1. A fluorescent light phantom device comprising:
a phantom support comprising a plurality of fluorescent light phantom containers; and
a plurality of fluorescent light phantoms each of which is constituted of a medium, which reproduces at least one of light scattering and light absorption of an object to be measured, and a fluorescent coloring matter contained in the medium of a predetermined concentration and is stored in the plurality of fluorescent light phantom containers,
wherein one of the plurality of fluorescent light phantoms is stored in each of the plurality of the fluorescent light phantom containers,
wherein concentration of the fluorescent coloring matter contained in each of the plurality of fluorescent light phantoms is different for each of the plurality of fluorescent light phantoms,
wherein material of the fluorescent coloring matter contained in each of the plurality of fluorescent light phantoms is the same for the plurality of fluorescent light phantom containers, and
wherein the phantom support further has a standard phantom container and further has a standard phantom, which is constituted of the medium and is stored in the standard phantom container.

2. The fluorescent light phantom device according to claim 1,
wherein the phantom support and one of the plurality of fluorescent light phantoms are formed by epoxy resin.

3. The fluorescent light phantom device according to claim 1,
wherein the medium includes:
at least one kind of scattered particles selected from the group consisting of titanium dioxide particles, silica particles, polymer minute particles, alumina, quartz glass minute particles and lipid minute particles; and
at least one light absorbing substance selected from the group consisting of a pigment and a dye.

4. The fluorescent light phantom device according to claim 1, wherein the fluorescent coloring matter is indocyanine green.

5. A method of evaluating a concentration of a fluorescent coloring matter in a living body, comprising steps of:
introducing the fluorescent coloring matter into the living body,
disposing a fluorescent light phantom in the vicinity of the living body with the device according to claim 1, wherein the fluorescent light phantom includes the fluorescent coloring matter;
irradiating the living body and the fluorescent light phantom device with excitation light; and
detecting first fluorescent light from the fluorescent coloring matter introduced in the living body and second fluorescent light from the fluorescent coloring matter included in the fluorescent light phantom,
comparing an intensity of the first fluorescent light with an intensity of the second fluorescent light.

6. A fluorescent light phantom device comprising:
a phantom support comprising a plurality fluorescent light phantom containers; and
a plurality of fluorescent light phantoms stored in the fluorescent light phantom container,
wherein each of the plurality of fluorescent light phantoms has:
a surface layer dummy, which is constituted of a medium that reproduces at least one of light scattering and light absorption of an object to be measured and is disposed at a surface layer of one of the plurality of fluorescent light phantom containers;
a deep layer dummy, which is constituted of the medium and is disposed at a deep layer of the fluorescent light phantom container; and
a tabular phantom, which is constituted of the medium and a fluorescent coloring matter contained in the medium and is disposed at one of the plurality of the fluorescent light phantom containers container to be held between the surface layer dummy and the deep layer dummy,
wherein one of the plurality of fluorescent light phantoms is stored in each of the plurality of the fluorescent light phantom containers,
wherein the tabular phantom has equivalent thicknesses in the respective plurality of fluorescent light phantoms, contains the fluorescent coloring matter of equivalent concentrations, and is disposed at a different depth in each of the plurality of fluorescent light phantoms,
wherein material of the fluorescent coloring matter contained in each of the plurality of fluorescent light phantoms is the same for the plurality of fluorescent light phantom containers, and
wherein the phantom support further has a standard phantom container and further has a standard phantom, which is constituted of the medium and is stored in the standard phantom container.

7. A fluorescent light phantom device,
wherein fluorescent light phantom devices according to claim 6 in which the plurality of the fluorescent light phantom containers are arranged in a row are arranged in a plurality of rows so that the fluorescent light phantoms are arranged in a matrix form, and
wherein concentration of the fluorescent coloring matter contained in the tabular phantom is different for each row.

* * * * *